United States Patent
Redko et al.

(10) Patent No.: US 11,773,128 B2
(45) Date of Patent: Oct. 3, 2023

(54) ELECTROCATALYTIC SYNTHESIS OF DIHYDROCHALCONES

(71) Applicant: BOARD OF TRUSTEES OF MICHIGAN STATE UNIVERSITY, East Lansing, MI (US)

(72) Inventors: Mikhail Redko, Ann Arbor, MI (US); Christopher M. Saffron, Okemos, MI (US); James E. Jackson, Haslett, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 6 days.

(21) Appl. No.: 17/598,590

(22) PCT Filed: Mar. 27, 2020

(86) PCT No.: PCT/US2020/025192
§ 371 (c)(1),
(2) Date: Sep. 27, 2021

(87) PCT Pub. No.: WO2020/198578
PCT Pub. Date: Oct. 1, 2020

(65) Prior Publication Data
US 2022/0089630 A1    Mar. 24, 2022

Related U.S. Application Data

(60) Provisional application No. 62/825,303, filed on Mar. 28, 2019.

(51) Int. Cl.
C25B 3/05    (2021.01)
C25B 3/25    (2021.01)
(Continued)

(52) U.S. Cl.
CPC .............. *C07H 15/207* (2013.01); *C25B 3/25* (2021.01); *C25B 9/19* (2021.01)

(58) Field of Classification Search
CPC .................................... C25B 3/25; C25B 3/05
(Continued)

(56) References Cited

U.S. PATENT DOCUMENTS 3,087,821 A    4/1963    Horowitz et al.
3,364,196 A    1/1968    Feldman et al.
(Continued)

FOREIGN PATENT DOCUMENTS

CN    1305743 A    8/2001
CN    101643485 A    2/2010
(Continued)

OTHER PUBLICATIONS

Manthey et al., "Concentrations of Hesperidin and Other Orange Peel Flavonoids in Citrus Processing Byproducts," Journal of Agricultural and Food Chemistry (Mar. 19, 1996), vol. 44, No. 3, pp. 811-814. (Year: 1996).*
(Continued)

*Primary Examiner* — Edna Wong
(74) *Attorney, Agent, or Firm* — MARSHALL, GERSTEIN & BORUN LLP

(57) ABSTRACT

The disclosure relates to methods of forming a dihydrochalcone using electrocatalytic dehydrogenation. In particular, the disclosure relates to methods of forming a dihydrochalcone electrocatalytically hydrogenating (ECH) a reactant compound over a catalytic cathode in a reaction medium having a non-alkaline pH value, thereby forming a dihydrochalcone product; wherein the reactant compound has a structure according to Formula (I). The method can be used to prepare dihydrochalcone sweeteners, such as, for
(Continued)

example, naringin dihydrochalcone and neohesperidin dihydrochalcone.

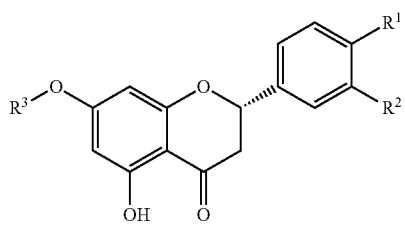

(I)

43 Claims, 5 Drawing Sheets

(51) Int. Cl.
C07H 15/207 (2006.01)
C25B 9/19 (2021.01)
(58) Field of Classification Search
USPC .................. 205/437, 445, 446, 455, 459
See application file for complete search history.

(56) References Cited

U.S. PATENT DOCUMENTS

| | | |
|---|---|---|
| 3,375,242 A | 3/1968 | Horowitz et al. |
| 4,087,558 A | 5/1978 | Linke et al. |
| 5,919,349 A | 7/1999 | Huber et al. |
| 7,183,444 B2 | 2/2007 | Kuhn et al. |
| 9,951,431 B2 | 4/2018 | Jackson et al. |
| 2014/0110268 A1 | 4/2014 | Jackson et al. |
| 2015/0008139 A1 | 1/2015 | Saffron et al. |
| 2016/0024669 A1 | 1/2016 | Jackson et al. |

FOREIGN PATENT DOCUMENTS

| | | | | |
|---|---|---|---|---|
| CN | 102093441 A | | 6/2011 | |
| CN | 103334119 A | * | 10/2013 | ............... C07H 1/08 |
| CN | 103772455 A | | 5/2014 | |
| CN | 104119408 A | | 10/2014 | |
| CN | 105801636 A | | 7/2016 | |
| ES | 8603908 A1 | | 1/1986 | |
| JP | 50154261 | | 12/1975 | |
| KR | 10-2011-0088743 A | | 8/2011 | |
| WO | WO-2013/134220 A1 | | 9/2013 | |

OTHER PUBLICATIONS

Nazareno et al., "Catalytic Hydrogenation Reaction of Naringin-Chalcone. Study of the Electrochemical Reaction," Molecules (Mar. 2000), vol. 5, No. 3, pp. 589-590. (Year: 2000).*
Haluk et al., "Analyse Qualitative de la Reduction Electrolytique des Flavonolosides en Milieu Hydro-Organique," Chimie Analytique (Mar. 1971), vol. 53, No. 3, pp. 149-154. (Year: 1971).*
Garg et al., "Chemistry and Pharmacology of the Citrus Bioflavonoid Hesperidin," Phytotherapy Research (Dec. 2001) vol. 15, No. 8 , pp. 655-669. (Year: 2001).*
Molina-Calle et al., "Development and Application of a Quantitative Method for Determination of Flavonoids in Orange Peel: Influence of Sample Pretreatment on Composition," Talanta (Nov. 1, 2015), vol. 144, pp. 349-355. (Year: 2015).*
Esaki et al., "Preparation and Taste of Certain Glycosides of Flavanones and of Dihydrochalcones", *Bioscience, Biotechnology, and Biochemistry*, 58(8):1479-85 (1994).
Kometani et al., "Synthesis of Neohesperidin Glycosides and Naringin Glycosides by Cyclodextrin Glucanotransferase from an Alkalophilic Bacillus Species," *Bioscience, Biotechnology, and Biochemistry*, 60(4):645-649 (1996).
Konishi et al., "Synthesis of flavonoid glycosides. Part XIII. Synthesis and taste of naringenin 7-O-(2-O-?-L-lyxopyranosyl-?-D-galactopyranoside) and its dihydrochalcone derivative", *Agricultural and Biological Chemistry*, 47(7):1633-5 (1983).
Lei et al., "Enzymatic production of natural sweetener trilobatin from citrus flavanone naringin using immobilised a-L-rhamnosidase as the catalyst," *International Journal of Food Science and Technology*, 53:2097-2103 (2018).
Tsuji et al., "Kinetic and thermodynamic barriers to carbon and oxygen alkylation of phenol and phenoxide ion by the 1-(4-methoxyphenyl)ethyl carbocation", *J. Am. Chem. Soc.*, 125(50):15455-65 (2003) (Abstract Only).
Gutierrez et al., Hydrogenation of chaicones using hydrogen permeating through a Pd and palladized Pd electrodes, Electrochim. Acta, 55(20):5831-9 (2010).
Nazareno et al., Catalytic hydrogenation reaction of narigin-chalcone, Study of the electrochemical reaction, Molecules, 5:589-90 (2000)u.
International Application No. PCT/US20/25192, International Search Report and Written Opinion, dated Jun. 24, 2020.

* cited by examiner

ELECTROCATALYTIC SYNTHESIS OF DIHYDROCHALCONES

CROSS REFERENCE TO RELATED APPLICATION

This application is a National Stage application of International Application No. PCT/US20/25192, filed Mar. 27, 2020, which claims the benefit of U.S. Provisional Patent Application 62/825,303, filed Mar. 28, 2019, the entire disclosures of both of which are incorporated herein by reference.

STATEMENT OF GOVERNMENT INTEREST

None.

BACKGROUND OF THE DISCLOSURE

Field of the Disclosure

The disclosure relates to methods of forming dihydrochalcones using electrolytic hydrogenation. In particular, the methods include electrolytically hydrogenating a compound over a catalytic cathode in a reaction medium having a non-alkaline pH, wherein the compound has a structure of Formula (I):

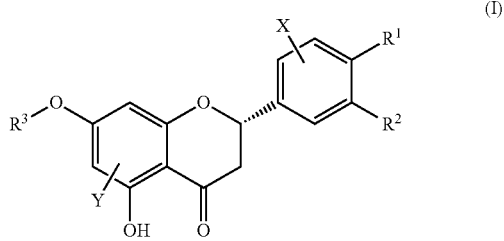

wherein each substituent is described in detail, below.

Brief Description of Related Technology

Hydrochalcones, e.g., dihydrochalcones, are a class of minor flavonoids that have two aromatic rings linked by a saturated three-carbon bridge. They occur with a limited, but heterogeneous, distribution in the plant kingdom. Two compounds of practical importance, belonging to this class, are artificial sweeteners—naringin dihydrochalcone and neohesperidin dihydrochalcone—whose molecular structures are shown below.

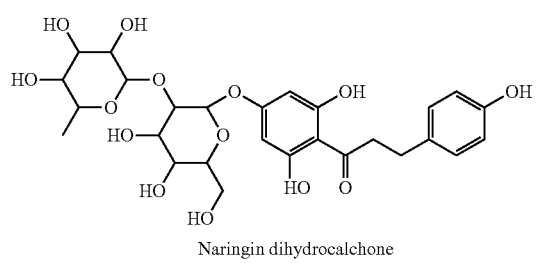

Naringin dihydrocalchone

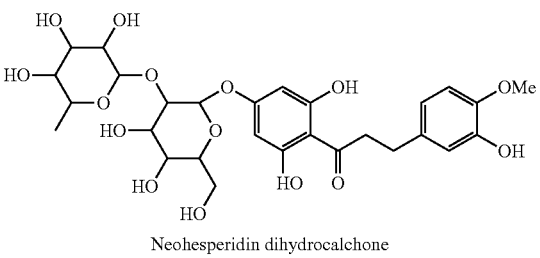

Neohesperidin dihydrocalchone

Naringin dihydrochalcone, sometimes abbreviated as naringin DC, is an artificial sweetener derived from naringin. The structure of naringin is shown below:

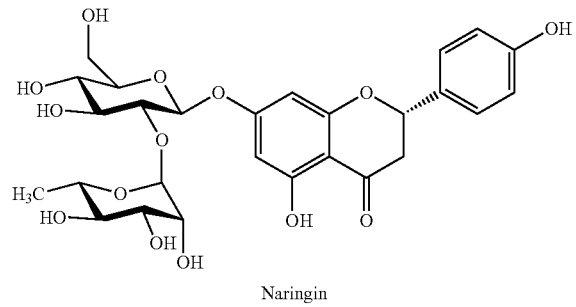

Naringin

Naringin occurs naturally in citrus fruits, especially in grapefruit, wherein naringin is responsible for the fruit's bitter taste. In commercial grapefruit production, the enzyme naringinase can be used to remove the bitterness created by naringin. When naringin is treated with potassium hydroxide or another strong base, and then catalytically hydrogenated, it becomes a dihydrochalcone that is roughly about 300 to about 1800 times sweeter than sugar at threshold concentrations.

Similarly, neohesperidin dihydrochalcone, sometimes abbreviated to neohesperidin DC or NHDC, is another artificial sweetener derived from citrus. NHDC is roughly about 1500 to about 1800 times sweeter than sugar at threshold concentrations, and around 340 times sweeter than sugar on a weight-for-weight basis. Like other highly sweet glycosides, such as glycyrrhizin and those found in stevia, NHDC's sweet taste has a slower onset than that of sugar, and lingers in the mouth for some time. Unlike aspartame, NHDC is stable to elevated temperatures and to acidic or basic conditions, and so it can be used in applications that require a long shelf life. NHDC itself can stay foodsafe for up to five years when stored in optimal conditions.

NHDC can be particularly effective in masking the bitter tastes of other compounds found in citrus, including limonin and naringin. Industrially, it is produced by extracting another bitter compound, neohesperidin, shown below, from the bitter orange, and then hydrogenating to make NHDC.

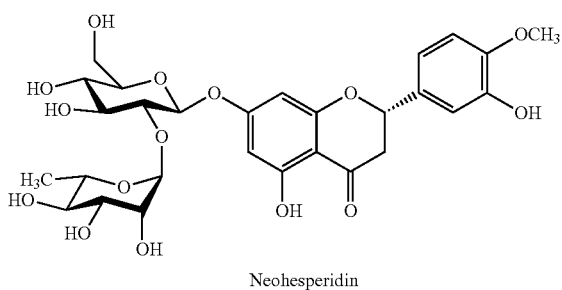

Neohesperidin

NHDC can be found in products such as alcoholic and non-alcoholic foods, savory foods, consumer products such as toothpaste and mouthwash, and condiments such as ketchup and mayonnaise. It is used in food as a flavor enhancer in concentrations of around about 4 ppm to about 5 ppm and as an artificial sweetener at around about 15 ppm to about 20 ppm Currently, industry utilizes enzymes to convert naringin into naringin DC, to reduce the bitter taste in juice products. However, enzymes are expensive and lead to high-priced juices and products, to the detriment of the customer. If only pure naringin DC is desired, as is the case when used to sweeten foods and other consumer products, naringin is first extracted from raw juice. A nickel catalyst, under high temperature and hydrogen gas pressure, is then used to convert naringin into naringin DC under undesirable alkaline solutions. Such severe operating conditions, and the need for molecular hydrogen lead to high costs, which again, are passed to the consumer.

Moreover, while the benzylic bonds in naringin and neohesperidin are known to undergo hydrogenolysis, this process is usually performed by reaction with hydrogen gas under 1 atm pressure using Pd/C catalyst. However, this approach also requires molecular hydrogen and the separation of dispersed Pd/C from the product mixture. Therefore, no industry is practicing this approach.

Accordingly, improved methods of preparing dihydrochalcones are needed.

SUMMARY

In one aspect, the disclosure provides a method of forming a dihydrochalcone, the method including electrocatalytically hydrogenating (ECH) a reactant compound over a catalytic cathode in a reaction medium having a non-alkaline pH value, thereby forming a dihydrochalcone product; wherein the reactant compound has a structure according to Formula (I):

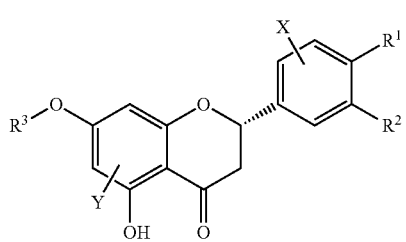

wherein each of $R^1$ and $R^2$ is independently selected from the group consisting of H, OH, or $C_{1-3}$ alkoxy, or $R^1$ and $R^2$ taken together with the atoms to which they are attached form a 5-6 membered cycloalkyl group or a 5-6 membered heterocycloalkyl group having 1 or 2 heteroatoms selected from N, O, and S; $R^3$ is H, $C_{1-3}$ alkyl, $C_{1-3}$ alkylene-$NR^aR^b$, $C_{0-3}$ alkylene-$PO_3H_2$, $C_{1-4}$ alkylene-$SO_3H$, $C_{1-3}$ alkylene-$CO_2H$, $C_{1-5}$ alkylene-OH, or a saccharide moiety, wherein each alkylene is optionally substituted with one or more of —$CO_2H$, —$NH_2$, —OH, and —$SO_3H$; each $R^a$ and $R^b$ is independently H or $SO_3H$; X is H, OH, $C_{1-3}$ alkyl, $NH_2$, halo, or $C_{1-3}$ alkoxy; and Y is H or $C_{1-3}$ alkyl. The X group can be independently selected at each of the possible substituent positions to be either the default hydrogen atom as illustrated or a substituent other than the illustrated hydrogen atom. Likewise, the Y group can be independently selected at each of the possible substituent positions to be either the default hydrogen atom as illustrated or a substituent other than the illustrated hydrogen atom. An initial reactant mixture generally includes the reaction medium and the reactant compound dissolved or dispersed therein. The reaction medium is suitably an aqueous reaction medium. Suitable reactant mixtures and reactant compounds can include those derived from various citrus sources. The dihydrochalcone product is formed in the reaction medium.

Various refinements of the disclosed methods of forming a dihydrochalcone are possible.

As provided herein, each of $R^1$ and $R^2$ can be H, OH, or $C_{1-3}$ alkoxy, or $R^1$ and $R^2$ taken together with the atoms to which they are attached form a 5-6 membered cycloalkyl group or a 5-6 membered heterocycloalkyl group having 1, 2, or 3 heteroatoms selected from N, O, and S. In refinements, $R^1$ is H. In refinements, $R^1$ is OH. In refinements, $R^1$ is $C_{1-3}$ alkoxy, for example —$OCH_3$, —$OCH_2CH_3$, —$O(CH_2)_2CH_3$, or —$OCH(CH_3)_2$. In various cases, $R^1$ is —$OCH_3$. In refinements, $R^2$ is H. In refinements, $R^2$ is OH. In refinements, $R^2$ is $C_{1-3}$ alkoxy, for example —$OCH_3$, —$OCH_2CH_3$, —$O(CH_2)_2CH_3$, or —$OCH(CH_3)_2$. In refinements, $R^1$ and $R^2$ taken together with the atoms to which they are attached form a 5-6 membered cycloalkyl group, for example, cyclopentyl or cyclohexyl. Unless specified otherwise, the 5-6 membered cycloalkyl group can be substituted or unsubstituted. In refinements, $R^1$ and $R^2$ taken together with the atoms to which they are attached form a 5-6 membered heterocycloalkyl group having 1 or 2 heteroatoms selected from N, O, and S, for example tetrahydrofuranyl, pyrrolindinyl, pyrazolindinyl, imidazolidinyl, piperidinyl, tetrahydropyranyl, thianyl, or piperazinyl. Unless specified otherwise, the 5-6 membered heterocycloalkyl group can be substituted or unsubstituted.

As provided herein, $R^3$ can be H, $C_{1-3}$ alkyl, $C_{1-3}$ alkylene-$NR^aR^b$, $C_{0-3}$ alkylene-$PO_3H_2$, $C_{1-4}$ alkylene-$SO_3H$, $C_{1-3}$ alkylene-$CO_2H$, $C_{1-5}$ alkylene-OH, or a saccharide moiety, wherein each alkylene is optionally substituted with one or more of —$CO_2H$, —$NH_2$, —OH, or —$SO_3H$. Suitable alkylene groups can include branch or unbranched, substituted or unsubstituted groups such as methylene (—$(CH_2)$—), ethylene (—$(CH_2)_2$—), propylene (—$(CH_2)_3$—), butylene (—$(CH_2)_4$—), and pentylene (—$(CH_2)_5$—). Each $R^a$ and $R^b$ is independently H or $SO_3H$. In refinements, $R^3$ is H, —$CH_3$, —$PO_3H_2$, —$(CH_2)_2NH_2$, —$(CH_2)_3NH_2$, —$(CH_2)_3$COOH, —CH(COOH) —$(CH_2)_2$—COOH, —$(CH_2)_2$—CH($NH_2$)—COOH, —$CH_2$COOH, —$(CH_2)_3PO_3H_2$, —$CH_2SO_3H$, —$(CH_2)_2SO_3H$, —$(CH_2)_3SO_3H$, —$(CH_2)_4SO_3H$, —$(CH_2)_2$—NH—$SO_3H$, —$(CH_2)_2$—CH($SO_3H$)—CH(OH)—$CH_2OH$, or —$(CH_2)_2$—CH($SO_3H$)—COOH.

In refinements, $R^3$ is a saccharide moiety, such as neohesperidose, glucose, rhamnose, glucopyranosyluronic acid, or rutinose. In some cases, $R^3$ is a neohesperidose moiety. In some cases, $R^3$ is a rutinose moiety.

As provided herein, X can be H, OH, $C_{1-3}$ alkyl, $NH_2$, halo, or $C_{1-3}$ alkoxy. The compound having a structure of Formula (I) can include an X substituent at any one or more of the available carbons on its corresponding aryl ring, which X substituents can be the same or different at different positions on the aryl ring. For example, there can be 0, 1, 2, or 3 aryl ring substituents in which X is a hydrogen atom, and the other aryl ring X substituents can be independently selected to be other than a hydrogen atom from the various indicated options. In refinements, X is H. In refinements, X is OH. In refinements X is $C_{1-3}$ alkyl, for example, methyl, ethyl, propyl, or isopropyl. In some cases, X is $CH_3$ (i.e. methyl). In refinements, X is $NH_2$. In refinements, X is halo, for example, F, Cl or Br. In some cases, X is Br. In refinements, X is 3 alkoxy, for example, —$OCH_3$, —$OCH_2CH_3$, —$O(CH_2)_2CH_3$, or —$OCH(CH_3)_2$. In some cases, X is —$OCH_3$.

As provided herein, Y is H or $C_{1-3}$ alkyl. The compound having a structure of Formula (I) can include a Y substituent at any one or more of the available carbons on its corresponding aryl ring, which Y substituents can be the same or different at different positions on the aryl ring. For example, there can be 0, 1, or 2 aryl ring substituents in which Y is a hydrogen atom, and the other aryl ring Y substituents can be independently selected to be other than a hydrogen atom from the various indicated options. In refinements, Y is H. In refinements, Y is $C_{1-3}$ alkyl, for example, methyl, ethyl, propyl, or isopropyl. In some cases, Y is $CH_3$ (i.e. methyl).

In refinements, the dihydrochalcone product has a structure according to Formula (II):

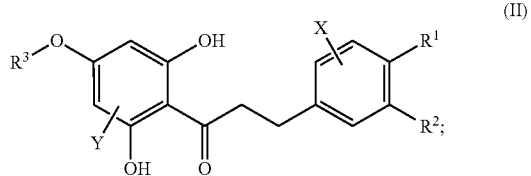

(II)

wherein $R^1$, $R^2$, $R^3$, X, and Y are as defined for Formula (I), above. For example, the $R^1$, $R^2$, $R^3$, X, and Y substituents can be selected from the above-defined groups but are generally the same in compounds according to Formula (I) and Formula (II) in a given reaction system.

Examples of suitable reactant compounds include, but are not limited to, naringenin, sakuranetin, isosakuranetin, eriodictyol, hesperetin, and any saccharide derivative thereof.

In refinements, $R^1$ is OH, $R^2$ is H, and $R^3$ is H or a saccharide moiety. That is, in refinements, the reactant compound includes a naringenin reactant and/or a saccharide derivative thereof. In some cases, $R^3$ is H (i.e. Formula (I) is naringenin). In some cases, $R^3$ is neohesperidose (i.e. Formula (I) is naringin). Accordingly, in refinements, the dihydrochalcone product includes a dihydrochalcone derived from naringenin or a saccharide derivative thereof (e.g. naringin), such as naringin dihydrochalcone.

In refinements, $R^1$ is OH, $R^2$ is H, and $R^3$ is CHs or a saccharide moiety. That is, in refinements, the reactant compound includes a sakuranetin reactant and/or a saccharide derivative thereof. In some cases, $R^3$ is CHs (i.e. Formula (I) is sakuranetin). Accordingly, in refinements, the dihydrochalcone product includes a dihydrochalcone derived from sakuranetin or a saccharide derivative thereof.

In refinements, $R^1$ is $OCH_3$, $R^2$ is H, and $R^3$ is H or a saccharide moiety. That is, in refinements, the reactant compound includes an isosakuranetin reactant and/or a saccharide derivative thereof. In some cases, $R^3$ is H (i.e. Formula (I) is isosakuranetin). In some cases, $R^3$ is a neohesperidose moiety (i.e. Formula (I) is poncirin). In some cases, $R^3$ is a rutinose moiety (i.e. Formula (I) is didymin). Accordingly, in refinements, the dihydrochalcone product includes dihydrochalcone derived from isosakuranetin or a saccharide derivative thereof (e.g. poncirin and/or didymin).

In refinements, $R^1$ is OH, $R^2$ is OH, and $R^3$ is H or a saccharide moiety. That is, in refinements, the reactant compound includes an eriodictyol reactant and/or a saccharide derivative thereof. In some cases, $R^3$ is H (i.e. Formula (I) is eriodictyol). In some cases, $R^3$ is a rutinose moiety (i.e. Formula (I) is eriocitrin). Accordingly, in refinements, the dihydrochalcone product includes an dihydrochalcone derived from eriodictyol or a saccharide derivative thereof (e.g. eriocitrin).

In refinements, $R^1$ is $OCH_3$, $R^2$ is OH, and $R^3$ is H or a saccharide moiety. That is, in refinements, the reactant compound includes a hesperetin reactant and/or a saccharide derivative thereof. In some cases, $R^3$ is H (i.e. Formula (I) is hesperetin). In some cases, $R^3$ is neohesperidose (i.e. Formula (I) is neohesperidin). Accordingly, in refinements, the dihydrochalcone product includes dihydrochalcone derived from hesperetin or a saccharide derivative thereof (e.g. neohesperidin), such as neohesperidin dihydrochalcone.

As provided herein, the method includes electrocatalytically hydrogenating (ECH) the reactant compound over a catalytic cathode in a reaction medium having a non-alkaline pH value. In refinements, the pH value of the reaction medium is 7 or less. For example, the pH value of the reaction medium can be about 7, 6.5, 6, 5.5, 5, 4.5, 4, 3.5, 3, 2, or 1, such as at least about 1, 2, 3, 4, or 5 and/or up to about 4, 4.5, 5, 5.5, 6, 6.5, or 7.

In refinements, the reaction medium is free of added base compounds. For example, in refinements, the reaction medium suitably contains less than about 0.5, 1, 3, or 5 wt % of added base compounds such as KOH, NaOH, $Ca(OH)_2$, $K_2CO_3$, $Na_2CO_3$, and the like, for example as initially provided in the reaction medium prior to ECH and/or in the reaction medium during and/or after ECH.

In refinements, prior to electrocatalytically hydrogenating the reactant compound, the reaction medium is free from a chalcone derivative having a structure according to Formula (III):

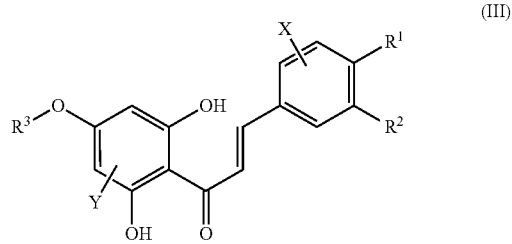

(III)

wherein $R^1$, $R^2$, $R^3$, X, and Y are as defined for Formula (I). For example, the $R^1$, $R^2$, $R^3$, X, and Y substituents can be selected from the above-defined groups but are generally the same in compounds according to Formula (I) and Formula (III) in a given reaction system. As used herein, the term "free from a chalcone derivative" means that the reaction medium suitably contains less than about 0.1, 0.5, 1, 3, or 5 wt % of the chalcone derivative, which can reflect that the original reactant compound has not undergone any preliminary conversion to a chalcone intermediate prior to application of a voltage potential for ECH, such as by treatment with a base or use of an alkaline reaction medium to partially or essentially completely shift the equilibrium from the reactant compound to the chalcone intermediate. Alternatively or additionally, the reaction medium suitably contains less than about 0.1, 0.5, 1, 3, or 5 wt % of the dihydrochalcone product (e.g., according to Formula (II) above) prior to electrocatalytically hydrogenating the reactant compound.

In refinements, prior to electrocatalytically hydrogenating the reactant compound, the reaction medium is free from at least one of (i) a chalcone having a structure or carbon skeleton according to Formula (IIIA) or a chalcone derivative having a structure or carbon skeleton according to Formula (IIIA) with one or more hydrogen atoms replaced with a different substituent, and (ii) a dihydrochalcone having a structure or carbon skeleton according to Formula (IIIB) or a dihydrochalcone derivative having a structure or carbon skeleton according to Formula (IIIB) with one or more hydrogen atoms replaced with a different substituent:

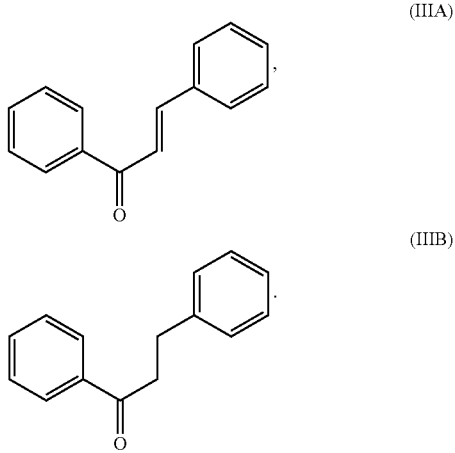

Similar to above, in refinements, the reaction medium suitably contains less than about 0.1, 0.5, 1, 3, or 5 wt % of the chalcone/chalcone derivative and/or less than about 0.1, 0.5, 1, 3, or 5 wt % of the dihydrochalcone/dihydrochalcone derivative, which can reflect that the original reactant compound has not undergone any preliminary conversion to an intermediate or product prior to application of a voltage potential for ECH.

In refinements, the catalytic cathode includes a catalytic metal. In refinements the catalytic metal includes Ru, Ni, Fe, Cu, Pt, Pd, Rh, Ir, Re, Os, Ag, Au, Co, Mo, Ga, W, Cr, Mn, mixtures thereof, alloys thereof, or combinations thereof. The metal catalyst can include pure or mixed carbides, silicides, pnictides, or chalcogenides of Cr, Mo, W, Ni, Co and Mn, such as, for example, $Ni_3N$, $Ni_3P$, $MoC$, $Mo_2C$, $WC$, $W_2C$, $MoSO_2$, $Co_xMoS_y$, or $Ni_xWS_y$, for example where each of x and y can range from 0-3. In general, and without intending to be bound by theory, the catalytic metal cleaves the desired C—O bond, but does not saturate the benzene and/or aryl rings, which should be preserved in the desired dihydrochalcone product.

In refinements, electrocatalytically hydrogenating the reactant compound includes (physically) contacting the reaction medium (i.e., containing the reactant compound therein) with the catalytic cathode; electrically contacting the reaction medium with an anode; and applying an electrical potential between the cathode and the anode to provide an electrical current therebetween and through the reaction medium, thereby hydrogenating the reactant compound in the reaction medium to form the dihydrochalcone product in the reaction medium. In some cases, electrical contact with anode can include a case where the anode is physically separated from/not in contact with the reaction medium, but current can flow between the anode and cathode, for example in a divided cell arrangement including an anode cell with the anode and anolyte (e.g., phosphoric acid, sulfuric acid, carbonic acid, and the like) separated by an ion-permeable membrane from a cathode cell with the cathode and reaction medium. In some cases, electrical contact with the anode can include a case where the anode is physically in contact with the reaction medium, for example in a single cell arrangement with the cathode, anode, and reaction medium all in the same compartment. Alternatively or additionally, in some cases, an electrolyzer reactor (e.g., including a single cell or divided cell electrode arrangement) may function with no anolyte added to the anodic compartment at all, so that the current will flow due to the flow of $H^+$ and $^-OH$ ions resulting from electrolytic dissociation of water. In this case, the energy consumption will increase due to the low electric conductance of pure water, resulting from low concentration of ions. However, use of pure water as electrolyte eliminates the potential addition and/or subsequent separation of one or more compounds from the reactant and product mixtures, thus reducing the cost and/or risk of providing a juice or other food product acceptably free from possibly contaminating substances.

In refinements, the reaction medium includes a feed material containing the reactant compound therein, such as (i) citrus extract, (ii) citrus biomass, and/or (iii) citrus juice containing one or more reactant compound therein. Suitable examples of citrus biomass include, but are not limited to peels, branches, leaves, trunks, roots, or combinations thereof (e.g., solid biomass in the reaction medium). In some cases, the citrus extract contains naringin and/or neohesperidin. In some cases, the citrus biomass includes naringin and/or neohesperidin. In some cases, the citrus juice contains naringin and/or neohesperidin;

In refinements, the citrus extract, the citrus biomass, and/or the citrus juice is derived from a citrus fruit. For example, in some cases, the citrus extract, citrus biomass, and/or citrus juice is derived from oranges, grapefruits, limes, lemons, mandarins, and combinations thereof. Generally, the given citrus fruit is extracted, peeled, and/or juiced/pressed to provide the corresponding citrus product with reactant compound therein.

In refinements, the reaction medium is free of dispersed catalyst. As used herein, "free of a dispersed catalyst" means that the reaction medium suitably contains less than about 0.1, 0.5, 1, 3, or 5 wt % of a particle catalyst, or other dispersible catalyst. Such catalysts can include the various metals and materials noted above, for example in the form of microparticles or nanoparticles themselves or supported on microparticle or nanoparticle support (e.g., palladium or other catalytic metal on particulate carbon support, denoted as Pd/C). Accordingly, in refinements no separation of dispersed catalyst from the reaction medium and product compounds is needed. Advantageously, the method can be carried out using a catalytically active material immobilized or otherwise fixedly attached to a conductive support which can collectively serve as a catalytic electrode. Alternatively, or additionally, a catalytically active material that is mechanically robust and highly porous can be used as the catalyst and electrode. For example, suitable catalysts include palladium deposited on a carbon cloth, Raney nickel or other skeletal metal catalyst, etc.

In refinements, the reaction medium is free of hydrogen. As used herein, "free of hydrogen" means that the reaction medium suitably contains less than about 0.1, 0.5, 1, 3, or 5 ppm of hydrogen ($H_2$) whether dissolved or dispersed as bubbles. Advantageously, no hydrogen gas is fed into the reactor.

In refinements, the reaction medium is free of added enzymes. That is, the reaction medium suitably contains less than about 0.1, 0.5, 1, 3, or 5 wt % of an enzyme which catalyzes any of: chalcone formation, dihydrochalcone formation, and dihydrochalcone conversion. Accordingly, no enzymes are needed for product conversion.

BRIEF DESCRIPTION OF THE DRAWINGS

For a more complete understanding of the disclosure, references should be made to the following detailed description and accompanying drawing wherein.

DETAILED DESCRIPTION

Figure 1:
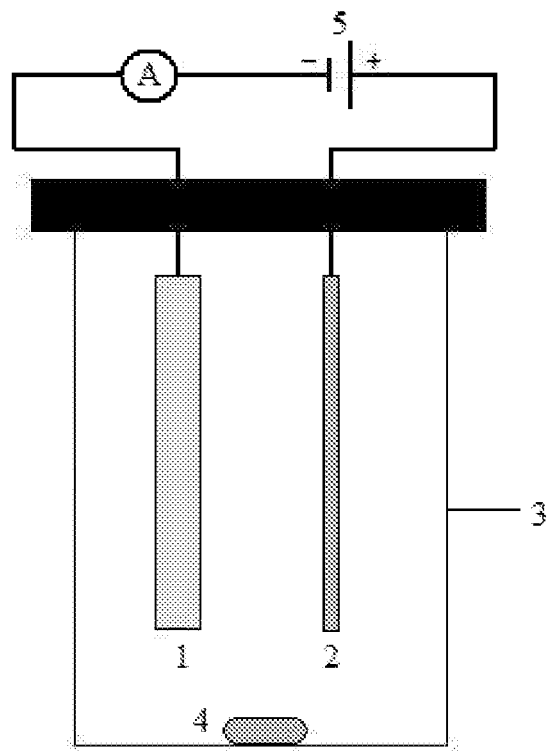
FIG. 1 illustrates an undivided electrochemical cell composed of cathode 1 and anode 2 in the same electrochemical chamber 3. A reactant medium (e.g., including a citrus material) is added into the electrochemical chamber 3 for the electrocatalytic hydrogenation. Power supply 5 provides electrons to cathode 1 for the reduction reaction, while the anode 2 releases electrons to the power supply. Stirring is used to enhance mass transfer with a magnetic stirring bar 4. An ammeter is used to measure the current.

The disclosure relates to methods of forming dihydrochalcones. In particular, the methods include electrocatalytically hydrogenating (ECH) a reactant compound over a catalytic cathode in a reaction medium having a non-alkaline pH value, thereby forming a dihydrochalcone product, the reactant compound has a structure according to Formula (I):

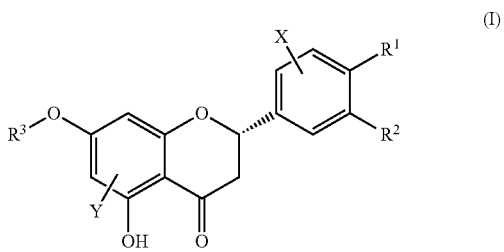

wherein each of $R^1$ and $R^2$ is H, OH, or $C_{1-3}$ alkoxy, or $R^1$ and $R^2$ taken together with the atoms to which they are attached form a 5-6 membered cycloalkyl group or a 5-6 membered heterocycloalkyl group having 1 or 2 heteroatoms selected from N, O, and S; $R^3$ is H, $C_{1-3}$alkylene-$NR^aR^b$, $C_{0-3}$alkylene-$PO_3H_2$, $C_{1-4}$alkylene-$CO_3H$, $C_{1-3}$alkylene-$CO_2H$ wherein the $C_{1-3}$alkylene is optionally substituted with one or more of —$CO_2H$, —$NH_2$, or —$SO_3H$; $C_{1-5}$alkylene-OH wherein the $C_{1-5}$alkylene is optionally substituted with one or more of —OH and —$SO_3H$; or a saccharide moiety; each $R^a$ and $R^b$ is independently selected from the group consisting of H and $SO_3H$; X is selected from the group consisting of H, OH, $C_{1-3}$alkyl, $NH_2$, halo, and $C_{1-3}$alkoxy; and Y is selected from the group consisting of H and $C_{1-3}$alkyl.

Chemical Definitions

As used herein, "alkyl" refers to straight chained and branched saturated hydrocarbon groups containing one to thirty carbon atoms, for example one to twenty carbon atoms, or one to ten carbon atoms. The term $C_n$ means the alkyl group has "n" carbon atoms. For example, $C_4$ alkyl refers to an alkyl group that has 4 carbon atoms. The term $C_{m-n}$ means the alkyl group has "m" to "n" carbon atoms. For example, $C_{1-3}$ alkyl refers to an alkyl group having a number of carbon atoms encompassing the entire range (i.e., 1 to 3 carbon atoms), as well as all sub groups (e.g., 1-3, 2-3, 1-2, 1, 2, and 3 carbon atoms). Nonlimiting examples of alkyl groups include, methyl, ethyl, n-propyl, and isopropyl. Unless otherwise indicated, an alkyl group can be an unsubstituted alkyl group or a substituted alkyl group.

As used herein, "alkylene" refers to a bivalent saturated aliphatic radical. The term $C_n$ means the alkylene group has "n" carbon atoms. For example, $C_{0-5}$ alkylene refers to an alkylene group having a number of carbon atoms encompassing the entire range (i.e., 0 to 5 carbon atoms) as well as all subgroups (e.g., 1-5, 2-5, 3-5, 4-5, 0-4, 1-4, 2-4, 3-4, 0-3, 1-3, 2-3, 0-2, 1-2, 0, 1, 2, 3, 4, 5, and 6 carbon atoms). An alkylene can branched or linear. Optionally, the alkylene can be substituted, for example, with one or more of —$CO_2H$, —$NH_2$, —OH, or —$SO_3H$ groups.

As used herein, "cycloalkyl" refers to an non-aromatic, aliphatic cyclic hydrocarbon group. The term $C_n$ means the cycloalkyl group has "n" carbon atoms. For example, $C_5$ cycloalkyl refers to a cycloalkyl group that has 5 carbon atoms in the ring. $C_{3-6}$ cycloalkyl refers to cycloalkyl groups having a number of carbon atoms encompassing the entire range (i.e., 3 to 6 carbon atoms), as well as all subgroups (e.g., 3-5, 3-4, 4-6, 4-5, 3, 4, 5, or 6 carbon atoms). Nonlimiting examples cyclopentyl and cyclohexyl. Unless otherwise indicated, a cycloalkyl group can be an unsubstituted cycloalkyl group or a substituted cycloalkyl group.

As used herein, "heterocycloalkyl" is defined similarly to cycloalkyl, except the ring contains one to three heteroatoms selected from N, O, and S. For example, a heterocycloalkyl group can be a 5-6 membered ring having 1 or 2 heteroatoms selected from N, O, and S, such as tetrahydrofuranyl, pyrrolindinyl, pyrazolindinyl, imidazolidinyl, piperidinyl, tetrahydropyranyl, thianyl, and piperazinyl.

As used herein, "alkoxy" is defined as —OR, wherein R is alkyl.

As used herein, "halo" is defined as fluoro, chloro, bromo, or iodo.

As used herein, a "saccharide moiety" is any mono-, di-, polysaccharide, or derivative of any of the foregoing, which can be ether-linked to the base reactant compound structure. Nonlimiting examples of saccharide moieties include glucose, neohesperidose, rhamnose, glucopyranosyluronic acid, and rutinose.

Methods of Forming Dihydrochalcones

Provided herein are methods of forming dihydrochalcones, such as naringin dihydrochalcone and neohesperidin dihydrochalcone. The methods include electrocatalytically hydrogenating (ECH) a reactant compound over a catalytic cathode in a reaction medium having a non-alkaline pH value, thereby forming a dihydrochalcone product. The reactant compound has a structure of structure according to Formula (I):

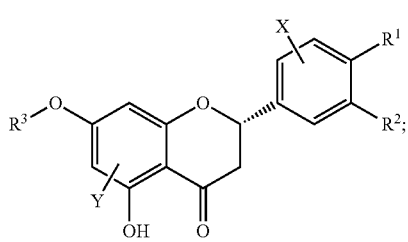

(I)

wherein the substituents are described in detail below. Examples of suitable reactant compounds include, but are not limited to, naringenin, sakuranetin, isosakuranetin, eriodictyol, hesperetin, and any saccharide derivative thereof. In refinements, the corresponding dihydrochalcone product has a structure according to Formula (II):

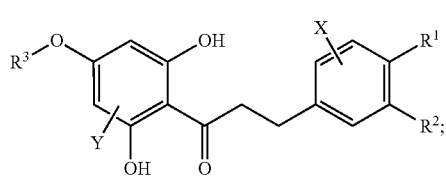

(II)

wherein the substituents are as defined for Formula (I), and are described in detail below.

Electrocatalytic hydrogenation (ECH) is a process that can be used in the hydrogenation, deoxygenation, and demethoxylation of aromatic compounds. Advantageously, ECH can be used to transform naringin and neohesperidin, by hydrogenolysis of the benzylic C—O bonds, into the sweeter naringin DC and NHDC. The methods of the disclosure can be used to convert naringin and/or neohesperidin over a catalytic cathode, for example containing Pd nanoparticles, to cause the benzylic C—O bond cleavage, as shown by Scheme 1, below. Unlike current laboratory and industrial processes, the methods of the disclosure do not require hydrogen gas, and they likewise do not require a dispersed catalyst (e.g., which would further entail separation and recycle), thus saving on cost. Moreover, the methods of disclosure can operate at low pressures, temperatures, and pH, thereby leading to lower costs, while being applicable for sweetening raw juice, unlike industrial approaches using, for example, nickel catalysts.

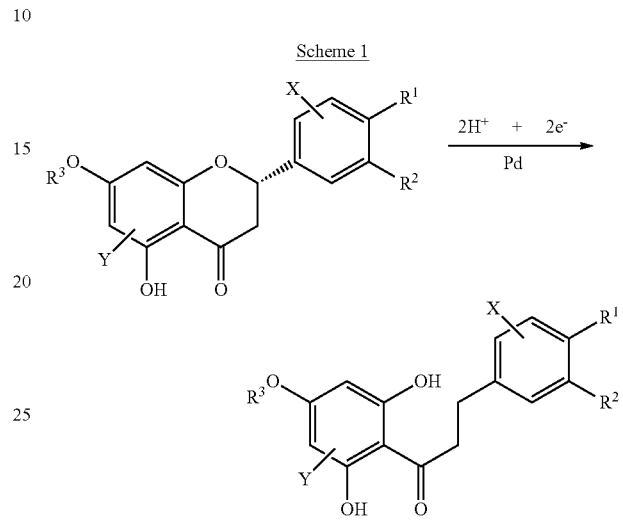

Scheme 1

The methods of the disclosure can also improve process safety. Traditional catalytic hydrogenation involves handling of highly flammable hydrogen gas, which can form explosive mixtures with air. Hydrogen storage and supply typically involves high pressures, which can significantly increase the cost and complexity of the corresponding equipment. In contrast, the methods of the disclosure can advantageously be performed at atmospheric pressures and ambient temperatures. The methods of the disclosure do not require gaseous hydrogen, and even if some hydrogen evolves in the process, it can safely be discharged into the atmosphere via thin metallic tubes, thereby preventing any chances of fire or explosion. Advantageously, by applying the methods of the disclosure to an industrial or commercial application, the ECH of naringin and/or neohesperidin into naringin and/or NH DC, respectively, can be performed in a continuous system, for example including a pump to continuously feed a reaction mixture to an ECH reaction vessel (e.g., a single- or two-chamber ECH electrochemical cell) driven by a suitable voltage source. A similar, but larger, installation can be used in an industrial process.

Electrocatalytic hydrogenation of the reactant compounds and corresponding mixtures can be operated in two different electrochemical cells: an undivided electrochemical cell and a divided electrochemical cell. Suitable electrochemical cells are described below. US Publication No. 2014/0110268 and US Publication No. 2015/0008139 are incorporated herein by reference and include further disclosure related to suitable electrolyzer reactors and associated electrochemical cells as well as suitable catalytic materials/metals and related electrode support structures.

An example of the undivided cell is shown in FIG. 1, where the cathode 1 and the anode 2 are in the same electrochemical chamber 3. In general, various materials can be used as the cathode, including aluminum, iron, zinc, copper, stainless steel, graphite, activated carbon cloth, but not limited to these materials. To avoid oxidation of reaction system compounds at the anode side, a sacrificial anode can be used, such as sacrificial nickel, but not limited to nickel. In other embodiments, the anode can be made of bulk materials including platinum wire, platinum mesh, platinized titanium mesh, stainless steel wire, stainless steel mesh and graphite rod. In an embodiment, the cathode can include an electrocatalytic electrode composition including catalytic metal particles deposited onto an activated carbon cloth substrate, for example including palladium catalytic particles immobilized on the substrate. In an embodiment, the cathode can include an electrocatalytic electrode composition including porous skeletal catalytic metal (e.g., Raney nickel) particles supported on an electrode material such as stainless steel. The reaction feed material can be used as the electrolysis solution, for example an aqueous- or other liquid-based medium including one or more citrus-based feed materials therein.

Figure 2:
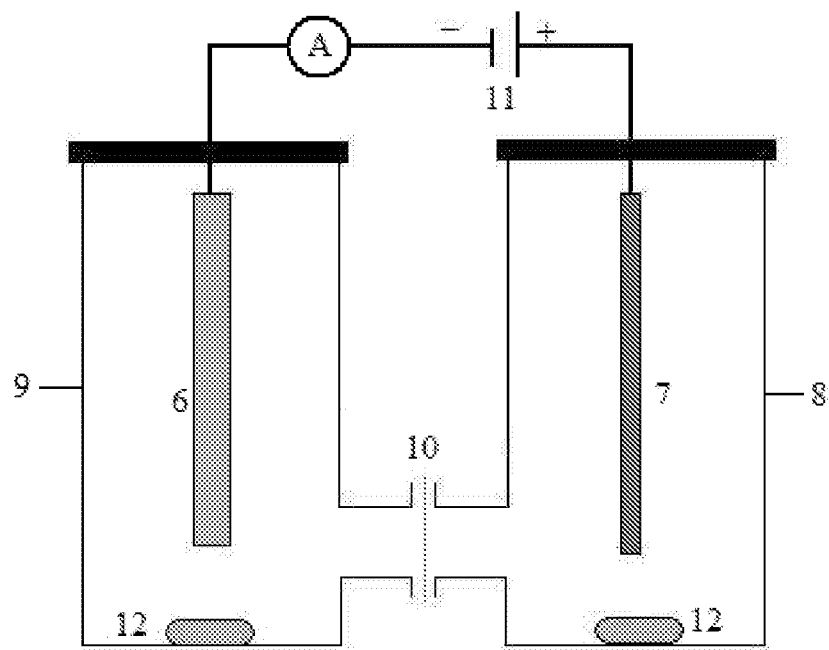
FIG. 2 illustrates a divided electrochemical cell composed of cathode 6 and anode 7 in different electrochemical chambers (anode chamber 8 and cathode chamber 9) separated by an ion exchange membrane 10. A reactant medium (e.g., including a citrus material) is added into the cathode chamber 9 and aqueous solution with electrolytes is put into the anode chamber 8. Power supply 11 provides voltage potential driving the electrons to the cathode 6. Magnetic stirring bar 12 is used to mix the solution to enhance mass transfer. An ammeter is used to measure the current.

An example of the divided cell is shown in FIG. 2. The anode chamber 8 and the cathode chamber 9 are separated by an ion exchange membrane 10. NAFION membranes, such as NAFION 115 and NAFION 117, are suitable (available from Dupont), but other membranes can be used as well, for example based on sulfonated tetrafluoroethylene-based fluoropolymer-copolymers or otherwise. Similar to above, the cathode 6 in the divided cell can include aluminum, iron, zinc, copper, stainless steel, graphite, or activated carbon cloth materials, for example including an activated carbon cloth material with catalytic metal particles deposited thereon or an electrocatalytic electrode composition with porous skeletal catalytic metal (e.g., Raney nickel) particles supported on an electrode material such as stainless steel. More generally, the catalytic metals which can be incorporated into the catalytic cathode structure include nickel, ruthenium, iron, copper, platinum, palladium, rhodium, iridium, rhenium, osmium, silver, gold, cobalt, molybdenum, gallium, titanium, manganese, zinc, vanadium, chromium, tungsten, and/or tin (e.g., including mixtures, alloys, or other combinations thereof). In some embodiments, the anode 7 can be made of bulk materials including platinum wire, platinum mesh, platinized titanium mesh, stainless steel wire, stainless steel mesh and graphite rod. Precious metals supported on high surface area material, such as platinum on activated carbon cloth, also can be used as an anode. The reaction feed material can be used as the cathode solution in the cathode chamber 9, for example an aqueous- or other liquid-based medium including one or more citrus-based feed materials therein. Aqueous solutions with electrolytes can be used as the anode solution in the anode chamber 8.

The various substituents $R^1$, $R^2$, $R^3$, X, and Y in the generic formulas for the reactants, intermediates, and/or products of the disclosed method are described in more detail below. A particular selection for a given substituent is generally consistent throughout the reaction in the various reactant, intermediate, and/or product counterparts. For example, a particular selection for $R^1$, $R^2$, and/or $R^3$ in reactant Formula (I) can correspond to the same selection in product Formula (II) and vice versa. Similarly, a particular selection and location for X and/or Y in reactant Formula (I) can correspond to the same selection and location in product Formula (II) and vice versa.

In various embodiments, each of $R^1$ and $R^2$ can be independently selected from the group consisting of H, OH, and $C_{1-3}$ alkoxy, or $R^1$ and $R^2$ taken together with the atoms to which they are attached can form a 5-6 membered cycloalkyl group or a 5-6 membered heterocycloalkyl group having 1-3 heteroatoms selected from N, O, and S.

In refinements, $R^1$ is H. In refinements, $R^1$ is OH. In refinements, $R^1$ is $C_{1-3}$ alkyoxy, for example, methoxy (—$OCH_3$), ethoxy (—$OCH_2CH_3$), propoxy (—$O(CH_2)_2CH_3$), or isopropoxy (—$OCH(CH_3)_2$). In refinements, $R^1$ is methoxy (—$OCH_3$).

In refinements, $R^2$ is H. In refinements, $R^2$ is OH. In refinements, $R^2$ is $C_{1-3}$ alkyoxy, for example, methoxy (—$OCH_3$), ethoxy (—$OCH_2CH_3$), propoxy (—$O(CH_2)_2CH_3$), or isopropoxy (—$OCH(CH_3)_2$).

In refinements, $R^1$ and $R^2$ taken together with the atoms to which they are attached form a 5-6 membered cycloalkyl group or a 5-6 membered heterocycloalkyl group having 1-3 heteroatoms selected from N, O, and S. In refinements, $R^1$ and $R^2$ taken together with the atoms to which they are attached form a 5-6 membered cycloalkyl group, for example, cyclopentyl or cyclohexyl. In refinements, $R^1$ and $R^2$ taken together with the atoms to which they are attached form cyclopentyl. In refinements, $R^1$ and $R^2$ taken together with the atoms to which they are attached form cyclohexyl. In refinements, the 5-6 membered cycloalkyl group is substituted. In refinements, the 5-6 membered cycloalkyl is unsubstituted.

In refinements, $R^1$ and $R^2$ taken together with the atoms to which they are attached form a 5-6 membered heterocycloalkyl group having 1-3 heteroatoms selected from N, O, and S, for example, tetrahydrofuranyl, pyrrolindinyl, pyrazolindinyl, imidazolidinyl, piperidinyl, tetrahydropyranyl, thianyl, or piperazinyl. In refinements, $R^1$ and $R^2$ taken together with the atoms to which they are attached form tetrahydrofuranyl. In refinements, $R^1$ and $R^2$ taken together with the atoms to which they are attached form pyrrolidinyl. In refinements, $R^1$ and $R^2$ taken together with the atoms to which they are attached form pyrazolindinyl. In refinements, $R^1$ and $R^2$ taken together with the atoms to which they are attached form imidazolidinyl. In refinements, $R^1$ and $R^2$ taken together with the atoms to which they are attached form piperidinyl. In refinements, $R^1$ and $R^2$ taken together with the atoms to which they are attached form tetrahydropyranyl. In refinements, $R^1$ and $R^2$ taken together with the atoms to which they are attached form thianyl. In refinements, $R^1$ and $R^2$ taken together with the atoms to which they are attached form piperazinyl. In refinements the 5-6 membered heterocycloalkyl group is substituted. In refinements, the 5-6 membered heterocycloalkyl group is unsubstituted.

In various embodiments, $R^3$ can be selected from the group consisting of H, $C_{1-3}$ alkyl, $C_{1-3}$ alkylene-$NR^aR^b$, $C_{0-3}$ alkylene-$PO_3H_2$, $C_{1-4}$ alkylene-$SO_3H$, $C_{1-3}$ alkylene-$CO_2H$, $C_{1-5}$ alkylene-OH, and a saccharide moiety.

In refinements, $R^3$ is H. In refinements, $R^3$ is $C_{1-3}$ alkyl, for example, methyl, ethyl, n-propyl, or isopropyl. In refinements, $R^3$ is methyl. In refinements, $R^3$ is ethyl. In refinements, $R^3$ is n-propyl or isopropyl.

In refinements, $R^3$ is $C_{1-3}$ alkylene-$NR^aR^b$. As provided herein, each $R^a$ and $R^b$ can be independently selected from the group consisting of H and $SO_3H$. In refinements, each of $R^a$ is H. In refinements, each of $R^a$ is $SO_3H$. In refinements, one of $R^a$ and $R^b$ is H and the other is $SO_3H$. In refinements, $R^3$ is $C_{0-3}$ alkylene-$PO_3H_2$. In refinements, $R^3$ is $C_{1-4}$ alkylene-$SO_3H$. In refinements, $R^3$ is $C_{1-3}$ alkylene-$CO_2H$. In refinements, $R^3$ is $C_{1-5}$ alkylene-OH. Each alkylene can be optionally substituted with one or more of —$CO_2H$, —$NH_2$, —OH, and —$SO_3H$. In some refinements wherein $R^3$ includes an alkylene group, the alkylene group is not substituted. In some refinements wherein $R^3$ includes an alkylene group, the alkylene group is substituted with one or more of —$CO_2H$, —$NH_2$, —OH, and —$SO_3H$.

In refinements, $R^3$ is selected from the group consisting of H, $CH_3$, $PO_3H_2$, $-(CH_2)_2NH_2$, $-(CH_2)_3NH_2$, $-(CH_2)_3COOH$, $-CH(COOH)-(CH_2)_2-COOH$, $-(CH_2)_2-CH(NH_2)-COOH$, $-CH_2COOH$, $-(CH_2)_3PO_3H_2$, $-CH_2SO_3H$, $-(CH_2)_2SO_3H$, $-(CH_2)_3SO_3H$, $-(CH_2)_4SO_3H$, $-(CH_2)_2-NH-SO_3H$, $-(CH_2)_2-CH(SO_3H)-CH(OH)-CH_2OH$, and $-(CH_2)_2-CH(SO_3H)-COOH$.

In refinements, $R^3$ is a saccharide moiety. For example, $R^3$ can be a saccharide moiety such as neohesperidose, glucose, rhamnose, glucopyranosyluronic acid, and rutinose. In refinements, $R^3$ is a neohesperidose moiety. In refinements, $R^3$ is a glucose moiety. In refinements, $R^3$ is a rhamnose moiety. In refinements, $R^3$ is a glucopyranosyluronic acid moiety. In refinements, $R^3$ is a rutinose moiety.

In various embodiments, X can be selected from the group consisting of H, OH, $C_{1-3}$ alkyl, $NH_2$, halo, and $C_{1-3}$ alkoxy. The compounds of the disclosure include up to three X substituents. In refinements, each X is H. In refinements, at least one X is H. In refinements, at least two X are H. In refinements, at least one X is OH. In refinements, at least one X is $C_{1-3}$ alkyl, for example, methyl, ethyl, n-propyl, or isopropyl. In refinements, at least one X is methyl ($CH_3$). In refinements, at least one X is $NH_2$. In refinements, at least one X is halo, such as F, Br, or Cl. In refinements, at least one X is Br. In refinements, at least one X is $C_{1-3}$ alkoxy, for example methoxy ($-OCH_3$), ethoxy ($-OCH_2CH_3$), propoxy ($-O(CH_2)_2CH_3$), or isopropoxy ($-OCH(CH_3)_2$). In refinements, at least one X is methoxy ($OCH_3$).

In various embodiments, Y can be selected from the group consisting of H and $C_{1-3}$ alkyl. The compounds of the disclosure include up to two Y substituents. In refinements, at least one Y is H. In refinements, each Y is H. In refinements, at least one Y is $C_{1-3}$ alkyl, for example, methyl, ethyl, n-propyl, or isopropyl. In refinements, at least one Y is methyl ($CH_3$). In refinements, one Y is H and the other Y is $C_{1-3}$ alkyl. In refinements, each Y is $C_{1-3}$ alkyl.

In refinements, $R^1$ is OH, $R^2$ is H, and $R^3$ is H or a saccharide moiety. For example, in refinements, Formula (I) includes the structure:

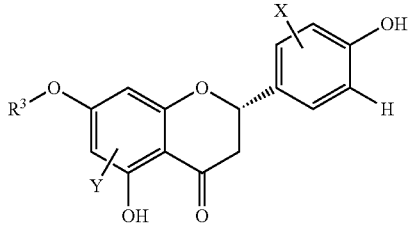

wherein $R^3$ is H or a saccharide moiety, and each X and Y can be as described herein. In refinements, $R^3$ is H. In refinements, $R^3$ is a saccharide moiety, such as a neohesperidose moiety.

In refinements, $R^1$ is OH, $R^2$ is H, and $R^3$ is $CH_3$ or a saccharide moiety. For example, in refinements, Formula (I) can be as illustrated above, where $R^3$ is $CH_3$ or a saccharide moiety, and each X and Y can be as described herein. In refinements, $R^3$ is $CH_3$. In refinements, $R^3$ is a saccharide moiety, such as a neohesperidose moiety.

In refinements, $R^1$ is $OCH_3$, $R^2$ is OH, and $R^3$ is H or a saccharide moiety. For example, in refinements, Formula (I) includes the structure:

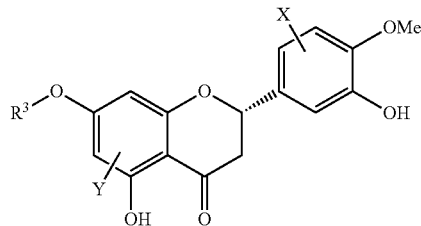

wherein $R^3$ is H or a saccharide moiety, and each X and Y can be as described herein. In refinements, $R^3$ is H. In refinements, $R^3$ is a saccharide moiety, such as a neohesperidose moiety.

In refinements, $R^1$ is $OCH_3$, $R^2$ is H, and $R^3$ is H or a saccharide moiety. For example, in refinements, Formula (I) includes the structure:

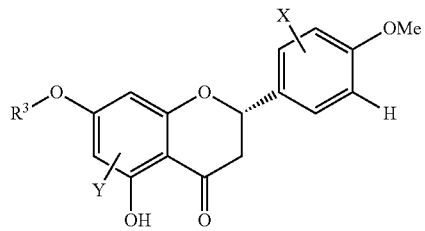

wherein $R^3$ is H or a saccharide moiety, and each X and Y can be as described herein. In refinements, $R^3$ is H. In refinements, $R^3$ is a saccharide moiety, such as a neohesperidose moiety.

In refinements, $R^1$ is OH, $R^2$ is OH, and $R^3$ is H or a saccharide moiety. For example, in refinements, Formula (I) includes the structure:

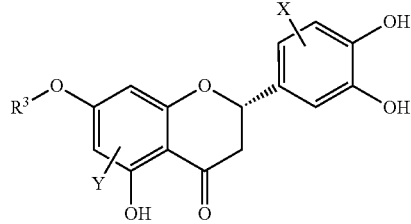

wherein $R^3$ is H or a saccharide moiety, and each X and Y can be as described herein. In refinements, $R^3$ is H. In refinements, $R^3$ is a saccharide moiety, such as a neohesperidose moiety.

As described herein, the methods can include electrocatalytically hydrogenating (ECH) a reactant compound over a catalytic cathode in a reaction medium having a non-alkaline pH value. In refinements, the pH value of the reaction medium is 7 or less, for example, at least about 1, 2, 3, 4, or 5 and/or up to about 4, 4.5, 5, 5.5, 6, 6.5, or 7.

As described herein, the reaction medium can be free of added base compounds, such as inorganic or organic bases. As used herein, the term "free of added base compounds," means that the composition suitably contains less than about 0.5, 1, 3, or 5 wt % of intentionally added base compounds, such as KOH, NaOH, Ca(OH)$_2$, K$_2$CO$_3$, Na$_2$CO$_3$, and the like, for example as initially provided in the reaction medium prior to ECH and/or in the reaction medium during and/or after ECH. In embodiments, the reaction medium is free of added KOH, NaOH, Ca(OH)$_2$, K$_2$CO$_3$, and Na$_2$CO$_3$.

In refinements, the reaction medium is free from a chalcone derivative having a structure according to Formula (III) prior to electrocatalytically hydrogenating the reactant compound:

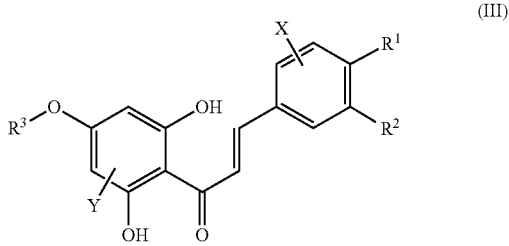

(III)

wherein each of R$^1$, R$^2$, R$^3$, X, and Y are as defined for Formula (I). That is, in refinements, the reaction medium suitably contains less than about 0.1, 0.5, 1, 3, or 5 wt % of the chalcone derivative. The absence, or limitation, of the chalcone derivative can reflect that the original reactant compound has not undergone any preliminary conversion to a chalcone intermediate, such as one having the structure of Formula (III), prior to the application of a voltage potential for ECH or other condition for ECH, such as by treatment with a base or use of an alkaline reaction medium to partially or essentially completely shift the equilibrium from the reactant compound to the chalcone intermediate. Alternatively or additionally, the reaction medium can suitably contain less than about 0.1, 0.5, 1, 3, or 5 wt % of the dihydrochalcone product (e.g., according to Formula (II)) prior to electrocatalytically hydrogenating the reactant compound.

For example, in refinements, prior to electrocatalytically hydrogenating the reactant compound, the reaction medium is free of a chalcone having a structure according to Formula (IIIA) or a chalcone derivative having a structure according to Formula (IIIA) with one or more hydrogen atoms (e.g., on either one or both of the aromatic rings) replaced with a different substituent:

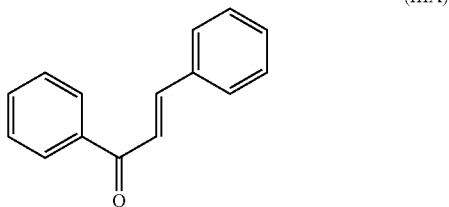

(IIIA)

In refinements, prior to electrocatalytically hydrogenating the reactant compound, the reaction medium is free of a dihydrochalcone having a structure according to Formula (IIIB) or a dihydrochalcone derivative having a structure according to Formula (IIIB) with one or more hydrogen atoms (e.g., on either one or both of the aromatic rings) replaced with a different substituent:

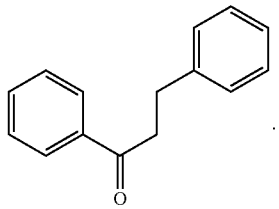

(IIIB)

In refinements, prior to electrocatalytically hydrogenating the reactant compound, the reaction medium is free from at least one of (i) a chalcone having a structure according to Formula (IIIA) or a chalcone derivative having a structure according to Formula (IIIA) with one or more hydrogen atoms replaced with a different substituent, and (ii) a dihydrochalcone having a structure according to Formula (IIIB) or a dihydrochalcone derivative having a structure according to Formula (IIIB) with one or more hydrogen atoms replaced with a different substituent.

In refinements, prior to electrocatalytically hydrogenating the reactant compound, the reaction medium is free from both of (i) a chalcone having a structure according to Formula (IIIA) or a chalcone derivative having a structure according to Formula (IIIA) with one or more hydrogen atoms replaced with a different substituent, and (ii) a dihydrochalcone having a structure according to Formula (IIIB) or a dihydrochalcone derivative having a structure according to Formula (IIIB) with one or more hydrogen atoms replaced with a different substituent.

The methods can include contacting a reactant mixture or reactant compound therein with a catalytic cathode, for example in a single or divided electrolytic cell. In refinements, the catalytic cathode includes a metal selected from the group consisting of Ru, Ni, Fe, Cu, Pt, Pd, Rh, Ir, Re, Os, Ag, Au, Co, Mo, Ga, W, Cr, Mn, mixtures thereof, alloys thereof, and combinations thereof. In embodiments, the catalytic cathode includes copper.

In refinements, electrocatalytically hydrogenating the reactant compound includes contacting the reaction medium with the catalytic cathode. For example, the reaction medium can be physically contacted with the catalytic cathode. In refinements, electrocatalytically hydrogenating the reactant compound includes electrically contacting the reaction medium with an anode. In refinements, electrocatalytically hydrogenating the reactant compound includes applying an electrical potential between the cathode and the anode to provide an electrical current therebetween and through the reaction medium, thereby hydrogenating the reactant compound in the reaction medium to form the dihydrochalcone product in the reaction medium.

The reaction medium can include a feed material for the compound including one or more citrus-based materials such as (i) a citrus extract, (ii) citrus biomass, and (iii) citrus juice. In refinements, the reaction medium includes a citrus extract. In embodiments, the reaction medium includes a citrus biomass, which can be any solid biomass present in the reaction medium. In refinements, the citrus biomass includes peels, branches, leaves, trunks, roots, and combinations thereof. In embodiments, the reaction medium includes citrus juice.

In refinements, the citrus extract, the citrus peel, and/or the citrus juice can include naringin and/or neohesperidin. More generally, the citrus-based feed materials can include one or more reactant compounds according to Formula (I).

In refinements, the citrus peel biomass and/or the citrus juice is derived from a citrus fruit. For example, in refinements, the citrus peel biomass and/or the citrus juice is selected from the group consisting of oranges, grapefruits, limes, lemons, mandarins, and combinations thereof.

Advantageously, the reaction medium can be free of dispersed catalyst. As used herein, "free of a dispersed catalyst" means that the reaction medium suitably contains less than about 0.1, 0.5, 1, 3, or 5 wt % of a particle catalyst, or other dispersible catalyst. Such catalysts can include the various metals and materials noted above for the catalytic cathode, for example in the form of microparticles or nanoparticles themselves or supported on microparticle or nanoparticle support (e.g., palladium or other catalytic metal on particulate carbon support, denoted as Pd/C). Accordingly, in refinements, no separation of dispersed catalyst from the reaction medium and product compounds is needed. Advantageously, the method can be carried out using a catalytically active material immobilized or otherwise fixedly attached to a conductive support which can collectively serve as a catalytic electrode. Alternatively, or additionally, a catalytically active material that is mechanically robust and highly porous can be used as the catalyst and electrode. For example, suitable catalysts include palladium deposited on a carbon cloth, Raney nickel or other skeletal metal catalyst, etc.

The reaction medium can be free of hydrogen. As used herein, "free of hydrogen" means that the reaction medium can suitably contain less than about 0.1, 0.5, 1, 3, or 5 ppm of hydrogen ($H_2$) whether dissolved or dispersed as bubbles. Advantageously, no hydrogen gas is fed into the reactor.

In refinements, the reaction medium is free of added enzymes. That is, the reaction medium suitably contains less than about 0.1, 0.5, 1, 3, or 5 wt % of an enzyme which catalyzes any one or more of: chalcone formation, dihydrochalcone formation, and dihydrochalcone conversion. Advantageously, no enzymes are needed for product conversion according to the methods of the disclosure.

EXAMPLES

Example 1: ECH of Naringin

Naringin (SIGMA-ALDRICH, 0.603 g), 10% Pd/C powder catalyst (ALFA AESAR, 0.092 g) and water (41.663 g) were placed into the cathodic side of a 2-sided custom made electrochemical cell, with a NAFION membrane separating the cathodic and anodic chambers. Phopshoric acid (4.180 g, 85% $H_3PO_4$ diluted with 44.692 g $H_2O$) was used as an anolyte. Copper wire was used as a cathode and platinum wire was used as an anode. The electrolysis was performed at room temperature using a constant voltage of E=18.2 V.

It was observed that the solubility of naringin in water was low, and that only a fraction of naringin dissolved (as observed by the presence of starting naringin remaining at the bottom of the flask). It was found that naringin (and naringin DC) were soluble in $d^6$-DMSO, which was used as the solvent in a subsequent electrolysis sample, in place of water in the process described above.

Figure 3:
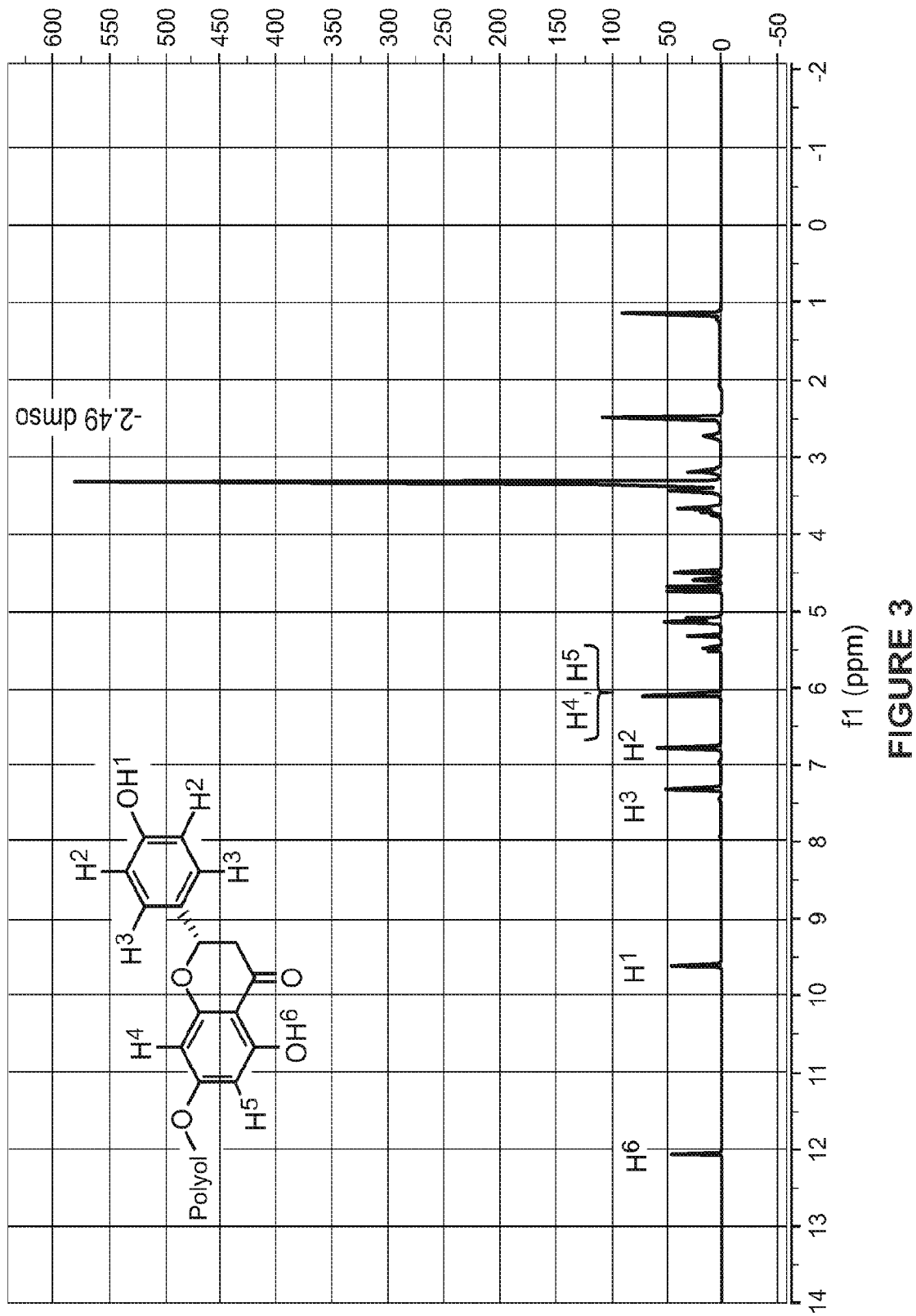
FIG. 3 is an $^1H$ NMR spectrum of commercial naringin dissolved in $d^6$-DMSO.
Figure 4:
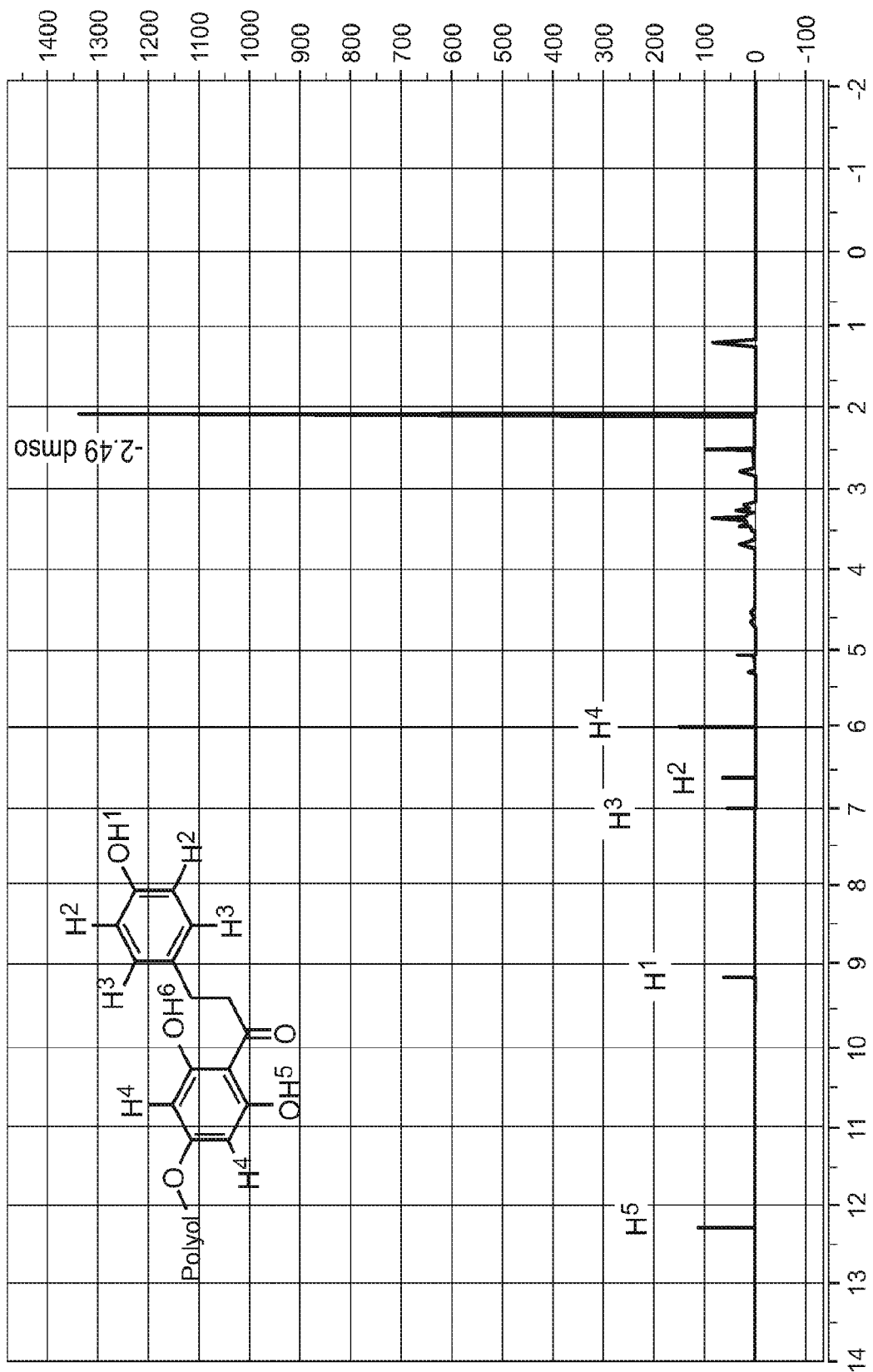
FIG. 4 is an $^1H$ NMR spectrum of commercial naringin dihydrochalcone dissolved in $d^6$-DMSO.
Figure 5:
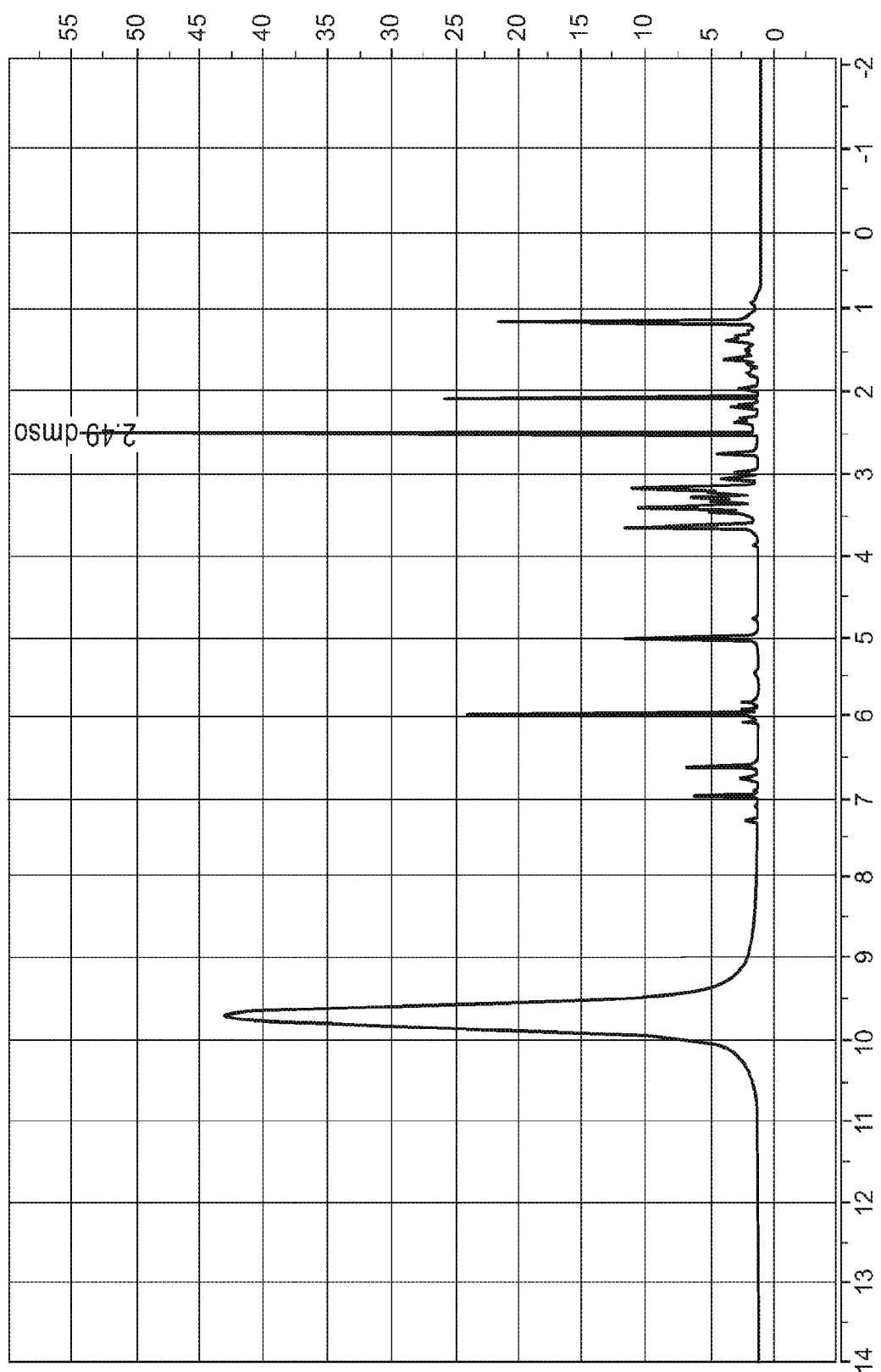
FIG. 5 is an $^1H$ NMR spectrum of a product mixture obtained according to the methods of the disclosure, dissolved in $d^6$-DMSO.

The $^1$H NMR spectra of commercial naringin and commercial naringin DC are shown in FIGS. 3 and 4, respectively. The $^1$H NMR spectrum of the final reaction mixture is shown in FIG. 5. The final reaction mixture spectrum was obtained by filtering a fraction of the aqueous catholyte solution, evaporating water at room temperature using flowing nitrogen gas, and dissolving the product in $d^6$-DMSO. Although the mass balance was not confirmed, the NMR spectra confirmed the conversion of naringin into naringin DC.

Figure 6:
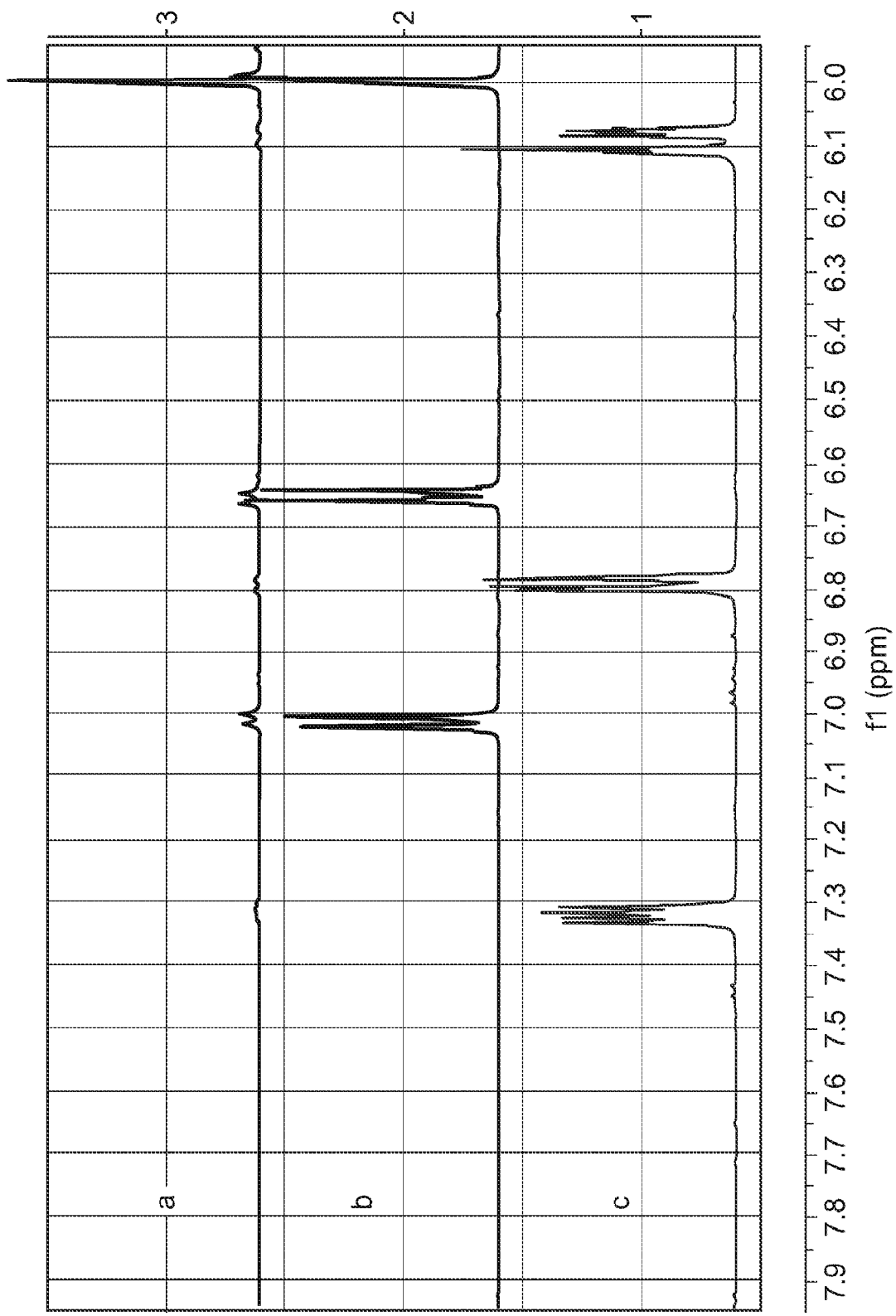
FIG. 6 is a fragment of an $^1H$ NMR spectrum of (a) a product mixture obtained according to the methods of the disclosure, dissolved in $d^6$-DMSO, (b) commercial naringin dihydrochalcone dissolved in $d^6$-DMSO, and (c) commercial naringin dissolved in $d^6$-DMSO.

FIG. 6 includes a superposition of the $^1$H NMR spectra of (a) the electrolysis product mixture obtained above, (b) a naringin DC product reference, and (c) a naringin reactant reference. FIG. 6 clearly illustrates the presence of both naringin and naringin DC in the product mixture. The molar ratio of naringin to naringin DC, obtained by the integration of the spectra, was about 1:3, indicating that the product mixture has more desired product than the starting material, thus confirming conversion of the reactant to the desired dihydrochalcone product.

Example 1 demonstrates that naringin DC was synthesized via electrocatalytic hydrogenation from naringin—a natural bitter tasting substance. This example demonstrates that ECH can be used to convert bitter compounds in citrus juice into highly potent sweeteners of much higher economic value.

Because other modifications and changes varied to fit particular operating requirements and environments will be apparent to those skilled in the art, the disclosure is not considered limited to the examples chosen for purposes of illustration, and covers all changes and modifications which do not constitute departures from the true spirit and scope of this disclosure.

Accordingly, the foregoing description is given for clearness and understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated by reference in their entirety. In case of conflict, the present description, including definitions, will control.

Throughout the specification, where the compounds, compositions, methods, and processes are described as including components, steps, or materials, it is contemplated that the compounds, compositions, methods, or processes can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed is:

1. A method of forming a dihydrochalcone, the method comprising:
    electrocatalytically hydrogenating (ECH) a reactant compound over a catalytic cathode in a reaction medium having a non-alkaline pH value, thereby forming a dihydrochalcone product; wherein:

the reactant compound has a structure according to Formula (I):

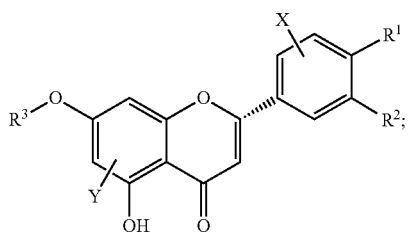

each of $R^1$ and $R^2$ is independently selected from the group consisting of H and OH, with the proviso that at least one of $R^1$ and $R^2$ is OH;

$R^3$ is selected from the group consisting of H, $C_{1-3}$ alkyl, $C_{1-3}$ alkylene-$NR^aR^b$, $C_{0-3}$ alkylene-$PO_3H_2$, $C_{1-4}$ alkylene-$SO_3H$, $C_{1-3}$ alkylene-$CO_2H$, $C_{1-5}$ alkylene-OH, and a saccharide moiety, wherein each alkylene is optionally substituted with one or more of —$CO_2H$, —$NH_2$, —OH, and —$SO_3H$;

each $R^a$ and $R^b$ is independently selected from the group consisting of H and $SO_3H$;

with a further proviso that $R^1$, $R^2$, and $R^3$ are selected from the group consisting of (a), (b), (c), (d), and (e) in which:
(a) $R^1$ is H, $R^2$ is as defined above, and $R^3$ is as defined above;
(b) $R^2$ is H, $R^1$ is as defined above, and $R^3$ is as defined above;
(c) $R^1$ is OH, $R^2$ is H, and $R^3$ is H or the saccharide moiety;
(d) $R^1$ is OH, $R^2$ is H, and $R^3$ is $CH_3$ or the saccharide moiety; and
(e) $R^1$ is OH, $R^2$ is OH, and $R^3$ is H or the saccharide moiety;

X is selected from the group consisting of H, OH, $C_{1-3}$ alkyl, $NH_2$, halo, and $C_{1-3}$ alkoxy;

Y is selected from the group consisting of H and $C_{1-3}$ alkyl; and, the dihydrochalcone product has a structure according to Formula (II):

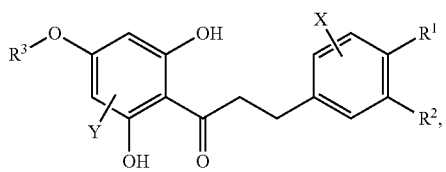

in which $R^1$, $R^2$, $R^3$, X, and Y are as defined for Formula (I).

2. The method of claim 1, wherein $R^1$ is H.
3. The method of claim 1, wherein $R^1$ is OH.
4. The method of claim 1, wherein $R^2$ is H.
5. The method of claim 1, wherein $R^2$ is OH.
6. The method of claim 1, wherein $R^3$ is selected from the group consisting of H, $CH_3$, $PO_3H_2$, —$(CH_2)_2NH_2$, —$(CH_2)_3NH_2$, —$(CH_2)_3COOH$, —$CH(COOH)$—$(CH_2)_2$—COOH, —$(CH_2)_2$—$CH(NH_2)$—COOH, —$CH_2COOH$, —$(CH_2)_3PO_3H_2$, —$CH_2SO_3H$, —$(CH_2)_2SO_3H$, —$(CH_2)_3SO_3H$, —$(CH_2)_4SO_3H$, —$(CH_2)_2$—NH—$SO_3H$, —$(CH_2)_2$—$CH(SO_3H)$—$CH(OH)$—$CH_2OH$, and —$(CH_2)_2$—$CH(SO_3H)$—COOH.

7. The method of claim 1, wherein $R^3$ is the saccharide moiety, and the saccharide moiety is selected from the group consisting of a neohesperidose moiety, a glucose moiety, a rhamnose moiety, a glucopyranosyluronic acid moiety, and a rutinose moiety.

8. The method of claim 7, wherein $R^3$ is the neohesperidose moiety.

9. The method of claim 7, wherein $R^3$ is the rutinose moiety.

10. The method of claim 1, wherein $R^1$ is OH, $R^2$ is H, and $R^3$ is H or the saccharide moiety.

11. The method of claim 10, wherein $R^3$ is the saccharide moiety, and the saccharide moiety is a neohesperidose moiety.

12. The method of claim 1, wherein $R^1$ is OH, $R^2$ is H, and $R^3$ is $CH_3$ or the saccharide moiety.

13. The method of claim 1, wherein $R^1$ is OH, $R^2$ is OH, and $R^3$ is the saccharide moiety.

14. The method of claim 1, wherein the pH value of the reaction medium is 7 or less.

15. The method of claim 1, wherein the reaction medium is free of added base compounds.

16. The method of claim 1, wherein prior to electrocatalytically hydrogenating the reactant compound, the reaction medium is free from a chalcone derivative having a structure according to Formula (III):

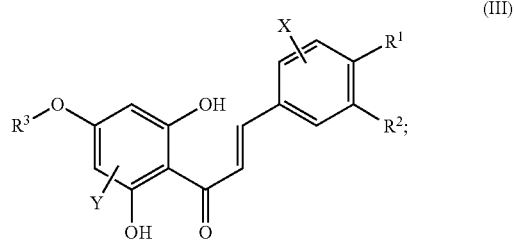

wherein $R^1$, $R^2$, $R^3$, X, and Y are as defined for Formula (I).

17. The method of claim 1, wherein prior to electrocatalytically hydrogenating the reactant compound, the reaction medium is free from at least one of (i) a chalcone having a structure according to Formula (IIIA) or a chalcone derivative having a structure according to Formula (IIIA) with one or more hydrogen atoms replaced with a different substituent, and (ii) a dihydrochalcone having a structure according to Formula (IIIB) or a dihydrochalcone derivative having a structure according to Formula (IIIB) with one or more hydrogen atoms replaced with a different substituent:

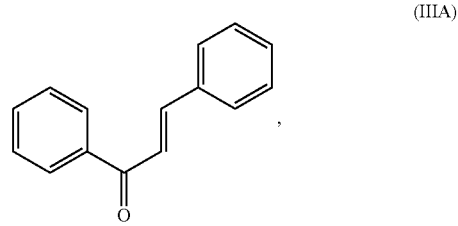 [SMILES: O=C(/C=C/c1ccccc1)c1ccccc1]

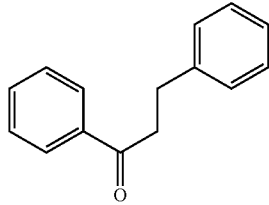

18. The method of claim 1, wherein the catalytic cathode comprises a catalytic metal selected from the group consisting of Ru, Ni, Fe, Cu, Pt, Pd, Rh, Ir, Re, Os, Ag, Au, Co, Mo, Ga, W, Cr, Mn, mixtures thereof, alloys thereof, and combinations thereof.

19. The method of claim 1, wherein electrocatalytically hydrogenating the reactant compound comprises:
physically contacting the reaction medium with the catalytic cathode;
electrically contacting the reaction medium with an anode; and
applying an electrical potential between the cathode and the anode to provide an electrical current therebetween and through the reaction medium, thereby hydrogenating the reactant compound in the reaction medium to form the dihydrochalcone product in the reaction medium.

20. The method of claim 1, wherein the reaction medium comprises a feed material for the reactant compound selected from the group consisting of: (i) citrus extract, (ii) citrus biomass, and (iii) citrus juice.

21. The method of claim 20, wherein the citrus extract, the citrus biomass, and/or the citrus juice comprises naringin and/or neohesperidin.

22. The method of claim 20, wherein:
the feed material is the citrus biomass; and
the citrus biomass is selected from the group consisting of peels, branches, leaves, trunks, roots, and combinations thereof.

23. The method of claim 20, wherein the citrus extract, the citrus biomass, and/or the citrus juice is derived from a citrus fruit selected from the group consisting of oranges, grapefruits, limes, lemons, mandarins, and combinations thereof.

24. The method of claim 1, wherein the reaction medium is free of dispersed catalyst.

25. The method of claim 1, wherein the reaction medium is free of hydrogen.

26. The method of claim 1, wherein the reaction medium is free of added enzymes.

27. A method of forming a dihydrochalcone, the method comprising:
electrocatalytically hydrogenating (ECH) a reactant compound over a catalytic cathode in a reaction medium having a non-alkaline pH value, thereby forming a dihydrochalcone product; wherein:
the reactant compound has a structure according to Formula (I):

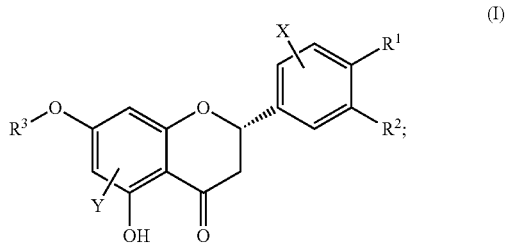

each of $R^1$ and $R^2$ is independently selected from the group consisting of H, OH, and $C_{1-3}$ alkoxy, or $R^1$ and $R^2$ taken together with the atoms to which they are attached form a 5-6 membered cycloalkyl group or a 5-6 membered heterocycloalkyl group having 1-3 heteroatoms selected from N, O, and S;
$R^3$ is selected from the group consisting of H, $C_{1-3}$ alkyl, $C_{1-3}$ alkylene-$NR^aR^b$, $C_{0-3}$ alkylene-$PO_3H_2$, $C_{1-4}$ alkylene-$SO_3H$, $C_{1-3}$ alkylene-$CO_2H$, $C_{1-5}$ alkylene-OH, and a saccharide moiety, wherein each alkylene is optionally substituted with one or more of —$CO_2H$, —$NH_2$, —OH, and —$SO_3H$;
each $R^a$ and $R^b$ is independently selected from the group consisting of H and $SO_3H$;
X is selected from the group consisting of H, OH, $C_{1-3}$ alkyl, $NH_2$, halo, and $C_{1-3}$ alkoxy;
Y is selected from the group consisting of H and $C_{1-3}$ alkyl;
the catalytic cathode comprises a catalytic metal selected from the group consisting of Ru, Ni, Fe, Cu, Pt, Pd, Rh, Ir, Re, Os, Ag, Au, Co, Mo, Ga, W, Cr, Mn, mixtures thereof, alloys thereof, and combinations thereof; and
the dihydrochalcone product has a structure according to Formula (II):

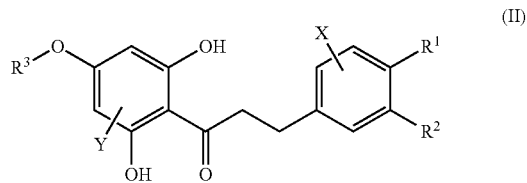

in which $R^1$, $R^2$, $R^3$, X, and Y are as defined for Formula (I).

28. The method of claim 27, wherein:
the reaction medium comprises a feed material for the reactant compound selected from the group consisting of: (i) citrus extract, (ii) citrus biomass, and (iii) citrus juice;
the citrus extract, the citrus biomass, and/or the citrus juice comprises naringin and/or neohesperidin; and
the citrus extract, the citrus biomass, and/or the citrus juice is derived from a citrus fruit selected from the group consisting of oranges, grapefruits, limes, lemons, mandarins, and combinations thereof.

29. The method of claim 28, wherein:
the feed material is the citrus biomass; and
the citrus biomass is selected from the group consisting of peels, branches, leaves, trunks, roots, and combinations thereof.

30. The method of claim 27, wherein $R^1$ is OH, $R^2$ is H, and $R^3$ is H, $CH_3$, or the saccharide moiety.

31. The method of claim 30, wherein:
R³ is the saccharide moiety, and the saccharide moiety is selected from the group consisting of a neohesperidose moiety, a glucose moiety, a rhamnose moiety, a glucopyranosyluronic acid moiety, and a rutinose moiety;
X is H; and
Y is H.

32. The method of claim 27, wherein R¹ is OCH₃, R² is OH, and R³ is H or the saccharide moiety.

33. The method of claim 32, wherein:
R³ is the saccharide moiety, and the saccharide moiety is selected from the group consisting of a neohesperidose moiety, a glucose moiety, a rhamnose moiety, a glucopyranosyluronic acid moiety, and a rutinose moiety;
X is H; and
Y is H.

34. The method of claim 27, wherein the reaction medium is free of at least one of added base compounds, dispersed catalyst, hydrogen, and added enzymes.

35. The method of claim 27, wherein prior to electrocatalytically hydrogenating the reactant compound, the reaction medium is free from a chalcone derivative having a structure according to Formula (III):

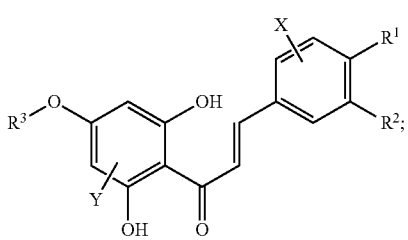

wherein R¹, R², R³, X, and Y are as defined for Formula (I).

36. The method of claim 27, wherein electrocatalytically hydrogenating the reactant compound comprises:
physically contacting the reaction medium with the catalytic cathode;
electrically contacting the reaction medium with an anode; and
applying an electrical potential between the cathode and the anode to provide an electrical current therebetween and through the reaction medium, thereby hydrogenating the reactant compound in the reaction medium to form the dihydrochalcone product in the reaction medium.

37. A method of forming a dihydrochalcone, the method comprising:
electrocatalytically hydrogenating (ECH) a reactant compound over a catalytic cathode in a reaction medium having a non-alkaline pH value, thereby forming a dihydrochalcone product; wherein:
the reactant compound has a structure according to Formula (I):

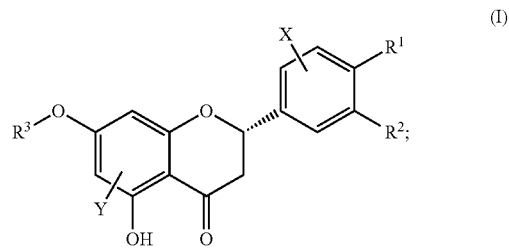

R¹, R², and R³ are selected from the group consisting of (a), (b), and (c) in which:
(a) R¹ is OH, R² is H, and R³ is H, CH₃, or a saccharide moiety;
(b) R¹ is OH, R² is OH, and R³ is H or a saccharide moiety; and
(c) (i) R¹ and R² taken together with the atoms to which they are attached form a 5-6 membered heterocycloalkyl group having 1-3 heteroatoms selected from N, O, and S; (ii) R³ is selected from the group consisting of H, $C_{1-3}$ alkyl, $C_{1-3}$ alkylene-NR$^a$R$^b$, $C_{0-3}$ alkylene-PO₃H₂, $C_{1-4}$ alkylene-SO₃H, $C_{1-3}$ alkylene-CO₂H, $C_{1-5}$ alkylene-OH, and a saccharide moiety, wherein each alkylene is optionally substituted with one or more of —CO₂H, —NH₂, —OH, and —SO₃H; and (iii) each R$^a$ and R$^b$ is independently selected from the group consisting of H and SO₃H;
X is selected from the group consisting of H, $C_{1-3}$ alkyl, NH₂, halo, and $C_{1-3}$ alkoxy;
Y is selected from the group consisting of H and $C_{1-3}$ alkyl; and
the dihydrochalcone product has a structure according to Formula (II):

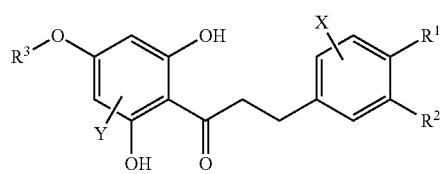

in which R¹, R², R³, X, and Y are as defined for Formula (I).

38. The method of claim 37, wherein:
the reaction medium comprises a feed material for the reactant compound selected from the group consisting of: (i) citrus extract, (ii) citrus biomass, and (iii) citrus juice;
the citrus extract, the citrus biomass, and/or the citrus juice comprises naringin and/or neohesperidin; and
the citrus extract, the citrus biomass, and/or the citrus juice is derived from a citrus fruit selected from the group consisting of oranges, grapefruits, limes, lemons, mandarins, and combinations thereof.

39. The method of claim 38, wherein:
the feed material is the citrus biomass; and
the citrus biomass is selected from the group consisting of peels, branches, leaves, trunks, roots, and combinations thereof.

40. The method of claim 37, wherein $R^1$ is OH, $R^2$ is H, and $R^3$ is H, $CH_3$, or the saccharide moiety.

41. The method of claim 40, wherein $R^3$ is the saccharide moiety.

42. The method of claim 37, wherein $R^1$ is OH, $R^2$ is OH, and $R^3$ is H or the saccharide moiety.

43. The method of claim 37, wherein $R^1$ and $R^2$ taken together with the atoms to which they are attached form the 5-6 membered heterocycloalkyl group having 1-3 heteroatoms selected from N, O, and S.

* * * * *